(12) United States Patent
Massoni

(10) Patent No.: US 6,818,022 B2
(45) Date of Patent: Nov. 16, 2004

(54) HAIR DYE COMPOSITION

(75) Inventor: Jack Massoni, Putnam Valley, NY (US)

(73) Assignee: Combe Inc., White Plains, NY (US)

(*) Notice: Subject to any disclaimer, the term of this patent is extended or adjusted under 35 U.S.C. 154(b) by 0 days.

(21) Appl. No.: 10/166,116

(22) Filed: Jun. 10, 2002

(65) Prior Publication Data

US 2002/0178514 A1 Dec. 5, 2002

Related U.S. Application Data

(63) Continuation of application No. 09/766,349, filed on Jan. 19, 2001, now abandoned.

(51) Int. Cl.$^7$ .............................................. A61K 7/13
(52) U.S. Cl. ..................... 8/405; 8/406; 8/410; 8/412; 8/580; 8/611
(58) Field of Search .......................... 8/405, 406, 410, 8/412, 580, 584, 611

(56) References Cited

U.S. PATENT DOCUMENTS 6,156,076 A * 12/2000 Casperson et al. ............. 8/406

2003/0226217 A1   12/2003   Bowes ........................ 8/405

OTHER PUBLICATIONS

Letter from Michael Teschner dated Jun. 2, 2004 with six attachments.

* cited by examiner

*Primary Examiner*—Yogendra N. Gupta
*Assistant Examiner*—Eisa Elhilo
(74) *Attorney, Agent, or Firm*—Hedman & Costigan, P.C.

(57) ABSTRACT

A hair dyeing composition which comprises the following ingredients:
(a) of an alkalizing amine;
(b) a multicomponent protective agent comprising a phosphated fatty alcohol, a hydrophobic agent and an alkyl ester of glucose;
(c) a non-ionic surfactant;
(d) a dye; and
(e) water.

9 Claims, No Drawings

HAIR DYE COMPOSITION

This application is a continuation of Ser. No. 09/766,349, filed Jan. 19, 2001 now abandoned.

BACKGROUND OF THE INVENTION

Hair dye compositions are routinely used to color human hair for diverse reasons. These compositions are usually used for the dyeing of head hair but are sometimes used for dyeing facial hair including moustaches, beards and sideburns. When surfactant-based prior art dyeing compositions have been employed, there have been incidents where the skin, particularly the skin underlying facial hair which is more sensitive than the scalp, has become irritated. In addition, it is well known that a small percentage of individuals who use hair dyes containing p-phenylenediamine and related compounds, ingredients essential in permanent hair dyes, can with repeated use develop an allergic sensitization potential to them. It is for this reason that U.S. law requires the labeling for all such hair dyes to instruct the user to perform a skin patch test to screen out those individuals who have developed such sensitization potential. Irritation of the skin compromises the natural protective functions of skin and thus increases the likelihood of allergic sensitization.

The applicant has found that the addition of a multicomponent hydrophobic material to the dye composition will reduce the possibility of skin irritation and possible sequelae. The applicant has found that the addition of a multicomponent hydrophobic agent will provide better dye coverage than a comparative dye composition which does not include the hydrophobic agent, and it will reduce the amount of temporary skin staining which is routinely encountered in the application of hair dyes.

The present invention is also directed to a hair coloring composition comprising the dye component of the invention and a developer component. In addition, the present invention includes a kit comprising at least two containers, one container containing the dye component of the invention and another container containing a developer component. The present invention is further directed to a method comprising applying the oxidative dye composition of the invention to hair, allowing the composition to remain ion contact with the hair until a desired hair color has been attained, and rinsing excess dye composition from the hair.

SUMMARY OF THE INVENTION

The invention provides novel hair dyeing compositions and methods which are based on the addition of a multicomponent protective agent comprising a hydrophobic material, a phosphated fatty alcohol and an alkyl ester of glucose to a hair dye composition in an amount that is effective to exert a protective effect on the skin which underlies the hair that is being dyed.

Accordingly, it is a primary object of the invention to provide a hair dye composition which includes a multicomponent protective agent which exerts a protective effect on the skin which underlies the hair being dyed.

It is also an object of the invention to provide a hair dye composition which includes a multicomponent protective agent which improves the dye coverage of the hair dye composition.

It is also an object of the invention to provide a hair dye composition which includes a multicomponent protective agent which reduces the temporary skin staining which is caused by certain dye compositions.

It is also an object of the invention to provide a hair dye composition which includes a multicomponent protective agent which reduces irritation and skin sensitization which may be caused by certain dye compositions.

These and other objects of the invention will become apparent from a review of the appended specification.

DETAILED DESCRIPTION OF THE INVENTION

The preferred dye compositions of the invention are formulated as a semi-solid gel or a semi-solid cream.

The novel hair dye compositions of the invention may comprise the following ingredients:
(a) from 0.01 to 6 wt % of an alkalizing agent;
(b) from 6 to 50 wt % of a multicomponent protective agent;
(c) from 5 to 30% by weight of a non-ionic surfactant;
(d) from 0.01 to 10 wt % of a dye; and
(e) from 50 to 90 wt % of water.

Preferred hair dye compositions according to the invention may comprise the following ingredients:
(a) from 1 to 3 wt % of an alkalizing agent;
(b) from, 13 to 30 wt % of a multicomponent protective agent;
(c) from 10 to 20 wt % of a non-ionic surfactant;
(d) from 0.01 to 5 wt % of a dye; and
(e) from 60 to 80 wt % of water.

The alkalizing amine component may be any of the commonly employed alkalizing agents which will adjust the pH of the dye, mixture to a pH of 6–10 and more preferably a pH in the range of 7.5–9. These alkalizing agents are those that are customarily used in hair dye compositions. Generally these materials comprise ammonium hydroxide, ammonia, compatible ammonia derivatives such as an alkylamine such as ethylamine, triethylamine, or alkanolamines such as monoethanolamine or triethanolamine or aminomethylpropanol; alkali metal carbonates, sodium hydroxide, potassium hydroxide and the like.

The multicomponent protective agent comprises a phosphated fatty alcohol, hydrophobic material and an alkyl ester of glucose. The phosphated fatty alcohol may comprise an ethoxylated or non-ethoxylated 8–23 carbon fatty alcohol or mixtures thereof. A typical phosphated alcohol is cetyl phosphate (CAS No. 3539-43-3). Another useful phosphated fatty alcohol is ceteth-8 phosphate which is a mixture of esters of phosphoric acid and a polyethylene glycol ether of cetyl alcohol. A hydrophobic material may comprise an amount of any material that is non-toxic and non-irritating to the skin, which is resistant to being washed off the skin with water and has a protecting effect on the skin underlying the hair which is to be dyed.

Examples of useful hydrophobic materials include liquid or semi-solid white or yellow petrolatum, lanolin, spermacetti, saturated and unsaturated $C_{14}$ to $C_{23}$ alcohols and mixtures thereof, cetyl esters wax, glyceryl esters of saturated and unsaturated $C_{14}$ to $C_{23}$ acids, saturated and unsaturated fatty acids such as $C_{14}$ to $C_{23}$ acids and their oligomers having 2 to 5 units, or purified hydrogenated or non-hydrogenated vegetable oils such as canola oil, soybean oil, corn oil, wheat germ oil, rice bran oil, and the like or mixtures thereof. If mixtures of hydrophobic agents are used, each may comprise from 20% to 50% by weight based on the total weight of the hydrophobic agents.

The third component of the multicomponent protective agent comprises an alkyl ester of glucose wherein the alkyl group is from 8 to 23 carbon atoms such as decyl polyglucose, cetyl polyglucose, lauryl polyglucose and the like or mixtures thereof. These materials are made by condensation of an alcohol and glucose. A preferred multi-component protective agent comprises white petrolatum, cetyl phosphate and cetyl polyglucose.

The preferred white petrolatum has a specific gravity of 0.815 to 0.880 at 60° C. and a melting point of between 38° and 60° C. which is stabilized with an antioxidant such as α-tocopherol.

Generally, the multicomponent protective agent will comprise from 10% to 60% by weight and more preferably from 30 to 40% by weight of the phosphated fatty alcohol; from 10 to 40 by weight and more preferably from 30 to 40 percent by weight of a hydrophobic agent; and from 10 to 40 by weight and more preferably from 30 to 40 percent by weight of a hydrophobic agent. The percents of each component are based on the total weight of the three components.

The non-ionic surfactants are used to emulsify the hydrophobic or non-aqueous components. They comprise well known materials and include polyethoxylated alcohols; polyethoxylated alkyl phenols; polyethoxylated organic ethers derived from fatty acids; polyethoxylated glyceryl esters and the like. Useful non-ionic surfactants are disclosed in U.S. Pat. No. 4,616,074 which is incorporated by reference. Preferred non-ionic surfactants include steareth-21 and polysorbate 80.

The dye component may be a typical dye component that is utilized in conventional oxidation hair dyes. These dyes include p-phenylenediamine derivatives, aminophenols, resorcinol and resorcinol derivatives, hydroquinone, catechol, 1,5-dinaphthalenediol, o-phenylenediamine, m-aminophenol and o-aminophenol. Examples of these dyes are described in U.S. Pat. Nos. 3,884,627; 4,311,478; 4,313,932; 4,685,931 and U.S. Pat. No. 4,323,360 all of which are incorporated by reference.

Optional components include gelling agents such as $C_{18-22}$ fatty acids; thickening agents such as $C_{18-22}$ fatty alcohols; antioxidants such as sodium sulfite; complexing agents such as mono, di, tri or tetrasodium EDTA may be added in effective amounts to provide a stable solution and fragrances which may be used in amounts which provide the desired effect.

The dye composition of the invention may be prepared by conventional mixing procedures. Generally it is preferred to combine the hydrophobic component or components to the non-ionic surfactant component or component and water to a suitable agitated mixing vessel which may be heated to a temperature of 50° to 90° C., and more preferably from 60° to 70° C. Mixing is carried out in such a manner as to minimize any foaming or air entrapment. After a substantially homogeneous mixture is obtained, the dye components are added at a slightly higher temperature, i.e. plus 5° to 10° C. The blended mixture is then cooled to a temperature of 25° to 55° C. and a fragrance is added with mixing. Thereafter the amine component is slowly added with gentle mixing of the combined components until the amine component is thoroughly dispersed.

Unless otherwise stated, all percentages used herein are by weight based on the total weight of the hair dye composition.

The developer phase may comprise a semi-solid gel or a semi-solid creme of the formula:
 (a) from 1 to 9 wt % of an oxidizing agent;
 (b) from 2 to 15 wt % of thickeners compatible with the oxidizing agent; and
 (c) from 97 to 75 wt % of water.

The oxidizing agent may be a compound such as urea peroxide, melamine peroxide, a perborate or a percarbonate. The thickeners that are compatible with the oxidizing agent would likely include a variety of non-ionic materials such as fatty alcohols, fatty esters, ethoxylated fatty alcohols, fatty amides and hydrocarbon waxes.

DESCRIPTION OF THE PREFERRED EMBODIMENTS

The following composition was prepared according to the present invention:

| | |
|---|---|
| water (deionized) | 69.060 |
| aminomethyl propanol (AMP-95, Angus) | 2.850 |
| cetaryl alcohol; dicetylphosphate; and ceteth-10 phosphate (Crodafros CES, Croda) | 4.500 |
| cetyl polyglucose (Montanov 68-EC, SEPPIC) | 4.000 |
| white petrolatum (White Fonoline, Witco) | 4.000 |
| canola vegetable oil (Emery 790 Fatty Acid) | 3.000 |
| oleyl alcohol | 3.000 |
| dilinoleic acid (Empol 1022, Henkel) | 3.000 |
| steareth-21 (BRIJ-721, ICI/Uniquena) | 3.000 |
| trisodium EDTA | 0.200 |
| erythorbic acid | 0.400 |
| sodium sulfite | 0.500 |
| p-phenylene diamine | 0.640 |
| m-aminophenol | 0.240 |
| p-aminophenol | 0.160 |
| 4-chlororesorcinol | 0.240 |
| 2-methylresorcinol | 0.260 |
| N-phenyl-p-phenylenediamine | 0.260 |
| resorcinol | 0.260 |
| fragrance (Charabot 15066) | 0.490 |
| | 100.000 |

The aminomethyl propanol are mixed with the hydrophobic components, the non-ionic surfactant components, the trisodium EDTA, erythorbic acid, sodium sulfite and water in a stainless steel vessel equipped with a sweep action mixer heated to a temperature of between 60° and 70° C. Mixing is carried out in such a manner as to minimize any foaming or air entrapment. After a solution is obtained and verified by sampling a bottom portion of the mixture, the phenylene diamine, phenolic and resorcinol ingredients are added at a temperature of 65° to 70° C. The blended mixture is then cooled to a temperature of 45° to 50° C. and the fragrance is added with mixing. Thereafter the aminomethyl propanol is slowly added with gentle mixing of the combined components until the amine component is thoroughly dispersed.

The composition of the invention has been tested by applying the dye composition to a group of 50 men with facial hair. On one-half of the beard a product was applied with no multicomponent protective agent while the other half used a formula that was similar to Example 1 with the following results: In all cases, the side of the face that was dyed with the formula which did not include a multicomponent protective agent displayed some degree of irritation in the form of burning, itching or redness. On the side that the formulation with the multicomponent protective agent, the irritation was lessened or was non-existent.

The foregoing description of a preferred embodiment of the invention has been presented for purposes of illustration and description. It is not intended to be exhaustive or to limit the invention precise form disclosed. Obvious modifications or variations are possible in light of the above teachings. All such obvious modifications and variations are intended to be within the scope of the appended claims.

What is claimed is:

1. A hair dyeing composition which comprises the following ingredients:
   (a) from 0.01 to 6 wt % of an alkalizing agent;
   (b) from 6 to 50 wt % of a multicomponent protective agent containing three ingredients a phosphated fatty alcohol, a hydrophobic agent and an alkyl ester of glucose;
   (c) from 5 to 30% by weight of a non-ionic surfactant;
   (d) from 0.01 to 10 wt % of a dye; and
   (e) from 50 to 90 wt % of water.

2. A hair dyeing composition as defined in claim 1 where the alkalizing agent is selected from the group consisting of ethanolamine, aminomethylpropanol and triethanolamine.

3. A hair dyeing composition as defined in claim 1 wherein the hydrophobic agent is selected from the group consisting of white petrolatum, a fatty alcohol, a fatty acid and mixtures thereof.

4. A hair dyeing composition as defined in claim 1 wherein the dye comprises a phenylenediamine, an aminophenol and a resorcinol.

5. A method of protecting the skin underlying hair which is being dyed from the effects of the hair dye composition, said method comprising addition to the hair dye composition an effective amount of a multicomponent protective agent containing three ingredients a phosphated fatty alcohol, a hydrophobic agent and an alkyl ester of glucose.

6. A method of protecting the skin underlying hair to be dyed as defined in claim 5 wherein the hydrophobic agent comprises white petrolatum, a fatty alcohol, a fatty acid or mixtures thereof.

7. In a hair dyeing composition comprising a surfactant, a hair dye package and an alkalizing agent, the improvement which comprises adding an amount of a multicomponent protective agent comprising a phosphated fatty alcohol, a hydrophobic agent and an alkyl ester of glucose which is effective to protect the skin under the hair which is dyed from the effects of the dye composition.

8. A hair dyeing composition as defined in claim 7 wherein the hydrophobic agent comprises white petrolatum, a fatty alcohol, a fatty acid or mixtures thereof.

9. A hair dyeing composition which consists essentially of the following ingredients:
   (a) from 0.01 to 6 wt % of an alkalizing agent selected from the group consisting of ethanolamine, aminomethylpropanol and triethanolamine;
   (b) from 6 to 50 wt % of a multicomponent protective agent comprising a phosphated fatty alcohol, a hydrophobic agent selected from the group consisting of white petrolatum, a fatty alcohol, a fatty acid and mixtures thereof with an alkyl ester of glucose;
   (c) from 5 to 30% by weight of a non-ionic surfactant;
   (d) from 0.01 to 10 wt % of a dye; and
   (e) from 50 to 90 wt % of water.

* * * * *